(12) United States Patent
Alexandre et al.

(10) Patent No.: US 7,559,917 B2
(45) Date of Patent: Jul. 14, 2009

(54) NEEDLELESS SYRINGE FUNCTIONING BY COMPRESSION OF THE RESERVOIR CONTAINING THE LIQUID ACTIVE PRINCIPLE

(75) Inventors: Patrick Alexandre, Gray (FR); Bernard Brouquieres, Toulon (FR); Bernard Pech, Paris (FR)

(73) Assignee: Crossject, Paris (FR)

( * ) Notice: Subject to any disclaimer, the term of this patent is extended or adjusted under 35 U.S.C. 154(b) by 510 days.

(21) Appl. No.: 10/332,487

(22) PCT Filed: Jul. 27, 2001

(86) PCT No.: PCT/FR01/02477

§ 371 (c)(1),
(2), (4) Date: Jan. 9, 2003

(87) PCT Pub. No.: WO02/09796

PCT Pub. Date: Feb. 7, 2002

(65) Prior Publication Data

US 2004/0039367 A1 Feb. 26, 2004

(30) Foreign Application Priority Data

Jul. 28, 2000 (FR) ................................. 00 09963

(51) Int. Cl.
*A61M 37/00* (2006.01)
(52) U.S. Cl. ..................................................... 604/143
(58) Field of Classification Search .................. 604/500, 604/143, 131, 141, 145, 148, 68–72, 140, 604/151, 135
See application file for complete search history.

(56) References Cited

U.S. PATENT DOCUMENTS

| | | | | |
|---|---|---|---|---|
| 2,699,166 A | * | 1/1955 | Dickinson, Jr. et al. | 604/70 |
| 2,764,977 A | | 10/1956 | Ferguson | |
| 4,941,880 A | * | 7/1990 | Burns | 604/143 |
| 5,730,723 A | * | 3/1998 | Castellano et al. | 604/143 |
| 6,096,002 A | * | 8/2000 | Landau | 604/68 |

FOREIGN PATENT DOCUMENTS

EP   0 792 174 B1   3/1999

* cited by examiner

*Primary Examiner*—Matthew F Desanto
(74) *Attorney, Agent, or Firm*—Oliff & Berridge, PLC

(57) ABSTRACT

The invention concerns the field of pre-filled and disposable needleless syringes, operating with a gas generator and used for intradermal, subcutaneous and intramuscular injections of a liquid active principle for therapeutic purposes in human and veterinary medicine. Said injection device (1) is mainly characterized in that it has a free pressuring space (26) around the reservoir (20) of the active principle (17) so that the gases produced by the gas generator (4) instantly penetrate said pressurizing space (26), compressing said reservoir (20) just before causing the plunger to move (18) to expel the liquid active principle (17). During said displacement, the reservoir (20) is subjected to a state of equal pressure.

12 Claims, 3 Drawing Sheets

NEEDLELESS SYRINGE FUNCTIONING BY COMPRESSION OF THE RESERVOIR CONTAINING THE LIQUID ACTIVE PRINCIPLE

The technical field of the invention is that of prefilled and disposable needleless syringes functioning with a gas generator and used for intradermal, subcutaneous and intramuscular injections of liquid active principle for therapeutic use in human or veterinary medicine.

More particularly, the invention concerns a cutaneous injection device comprising a body and intended to inject a liquid active principle contained in a tubular reservoir formed by a tube which is closed at its upstream end by a delivery plunger and which has, at its downstream end, an injection unit, this reservoir being lodged in the body of the injection device which includes, upstream of the plunger, a high-pressure gas generator making it possible to exert a pressure on this delivery plunger.

For the injection devices according to the invention, a liquid active principle consists of a more or less viscous liquid, or a mixture of liquid, or a gel. The active principle can be a solid dissolved in a suitable solvent for injection. It can also be represented by a powdered solid in more or less concentrated suspension in a suitable liquid. The particle size of the principle must be compatible with the diameter of the conduits in order to avoid blockages.

For prefilled syringes, the imperatives associated, on the one hand, with the long-term compatibility between the liquid active principle and the reservoir which contains it, and associated, on the other hand, with the regulatory control of the filling of said reservoir during the prefilling process, entail production of a reservoir which is substantially transparent and whose constituent material is compatible with the active principle to be injected.

Reservoirs made of glass satisfy this twin requirement. However, a limitation to the use of this type of reservoir rapidly becomes apparent, due mainly to the fact that the liquid active principle is expelled from the reservoir by the thrust of at least one solid plunger sliding in said reservoir, thereby inducing a very high internal pressure which may lead to said reservoir bursting open. A known way of guarding against this type of undesirable event is to use a surrounding sleeve for compression of the reservoir, able to counteract the internal pressure generated by the plunger and to preserve the integrity of the glass tube throughout the duration of the injection.

Devices for compressing the glass reservoir in needleless syringes intended to inject liquid active principle do already exist and have been the subject of several patents. Mention may be made, in particular, of the patent EP 0 792 174 which describes a glass vial designed to be used as a capsule in a needleless injector, said vial being placed in a permanent state of compression by means of a surrounding sleeve which can, for example, be made of polycarbonate. There are two drawbacks to this type of design: on the one hand, the production method requires a supplementary step involving inserting the sleeve around the vial, and, on the other hand, the vial is needlessly subjected to a permanent compressive force, including in the storage phase.

The patent U.S. Pat. No. 2,764,977 describes a hypodermic injection device using a reservoir which can be made of glass and is placed in a rubber sleeve. The compression of the reservoir by the sleeve takes place only at the time of functioning of the device and is provoked by the passage of a solid thrust plunger through the reservoir in order to expel the liquid active principle. Because the length of the sleeve is slightly greater than that of the reservoir, the plunger, when it begins its displacement, induces a pressure on the edge of the sleeve extending beyond the tube, this pressure being transmitted to the whole of the sleeve which reacts by compressing the reservoir. This type of device requires a high degree of homogeneity as regards the dimensioning and geometry of the components interacting with one another so as to obtain a perfect distribution of the forces exerted on the periphery of the reservoir. Finally, the patent U.S. Pat. No. 2,699,166 also discloses a hypodermic injection device involving a reservoir surrounded by a rubber sleeve. The compression of the reservoir by the sleeve takes place only at the time of functioning of the device, during which time a plunger is displaced and provokes, in a first stage, the arrival of an incompressible inert liquid in a space situated around the sleeve so as to compress said sleeve around the reservoir, then, in a second stage, the expulsion of the liquid active principle by pushing said principle in the reservoir. This type of device is made complex by the presence of a parallel hydraulic circuit and is made significantly heavier by the incompressible liquid of said circuit. Moreover, as the hydraulic circuit must not interfere directly with the expulsion of the active principle, it is necessary to use an operating mechanism which involves components of special geometry, necessitating special machining and consequently entailing higher costs.

The needleless syringe according to the invention has means for pneumatic compression of the reservoir containing the liquid active principle, making it possible to overcome all the aforementioned problems arising in the prior art. This is because these means are activated only at the time of the functioning of said syringes, and they do not therefore exert any stress on said reservoir in storage mode, thereby avoiding needless permanent stressing of the reservoir. Moreover, these means of compression do not involve any additional solid component specially produced to contribute to the compression of the reservoir, thus reducing the risks of poor functioning which arise when the number of components involved is increased. Finally, these means for compression of the syringes according to the invention are simple, direct and effective, in principle requiring only the presence of conduits connecting the gas generator to a free space situated around the reservoir. It was in fact discovered that it was possible to do without any surrounding sleeve for compression and protection, even in extreme cases when the injection device includes a glass tube with an average thickness of 2 to 2.5 mm and a pyrotechnic gas generator using propellant powders such as sporting powder or gun powder types permitting a pressure of over 400 bar.

The subject of the present invention is a cutaneous injection device comprising a body and intended to inject a liquid active principle contained in a tubular reservoir formed by a tube which is closed at its upstream end by a delivery plunger and which has, at its downstream end, an injection unit, this reservoir being lodged in the body of the injection device which includes, upstream of the plunger, a high-pressure gas generator making it possible to exert a pressure on this delivery plunger, characterized in that a space for pressurization by the gases of the generator is formed between the tubular reservoir and the inner wall of the body.

In this way, the gas generator has a dual function:
  expulsion of the liquid active principle by way of a plunger moved by the released gases,
  compression of the reservoir by accumulation of said gases in a space situated around the reservoir.

The displacement of the delivery plunger inside the reservoir instantaneously creates an internal overpressure which it is necessary to compensate by immediate compression of the reservoir. In this way, the reservoir is subjected to a state of equal pressure tending to cancel out the resultant stress exerted on it and eliminating any risk of fracturing. The reservoir can thus pass through the injection phase while maintaining its complete integrity despite the very high stresses in play. To be fully effective and to ensure a good margin of safety against the risk of fracturing of the reservoir, the compression of the reservoir must take place just before initiation of the internal pressure generated by the moving plunger, or at the latest at the same time. This technique takes up the principle of "free blocks" which is found in the field of propulsion and which consists, in the case of a block of propellant equipped with a central channel, of removing gases from said channel, when it is in combustion, and re-injecting them at its periphery in such a way as to equilibrate the pressures and avoid premature explosion due to an increase in the internal pressure associated with a decrease in the burning thickness.

This technique is for example entirely suitable for reservoirs made of glass which are not susceptible to deformation and which instead react in a binary mode, either by resisting the stresses without modifying, or by breaking without undergoing a transitory phase of deformation. Moreover, as a reservoir made of glass is more sensitive to tensile stress than to compressive stresses, it will much better resist the internal stresses by being compressed.

According to a first embodiment of the invention, the inner wall of the body includes at least three longitudinal ribs for centering the tubular reservoir, and the longitudinal ribs preferably include a shoulder for longitudinal wedging of the tubular reservoir. In this way, the reservoir is blocked in the syringe both along a transverse axis, by virtue of the longitudinal centering ribs holding it stable along its axis, and along a longitudinal axis by virtue of the wedging shoulder.

The tube is advantageously made of glass in order to satisfy the dual requirement of compatibility of the active principle with the material from which its reservoir is made, and of legibility for checking the filling of said reservoir.

The outer surface of the delivery plunger, directed toward the gas generator, preferably constitutes a deflector for deflecting the gases toward the pressurization space in such a way as to favor rapid accumulation of the gases toward the pressurization space just before the plunger has been able to begin to move, permitting compression of the reservoir before the generation of an internal overpressure in said reservoir. The end of the plunger directed toward the gas generator advantageously has a conical shape in order to optimize the flow of the gases around the reservoir by diverting said gases immediately toward the pressurization space.

The delivery plunger preferably extends above the tube and bears on the longitudinal ribs of the body.

The plunger preferably includes a starting point for rupture by shearing, which corresponds to the internal dimensions of the tube. In this way, the plunger has the role of a calibrated protective cap, making it possible to establish a threshold pressure level upstream of said plunger, beyond which it will burst, under a hollow punch effect, at the area of the starting point for rupture by shearing, in order to begin its travel through the reservoir. The starting point for rupture by shearing makes it possible to delay the start of the plunger in order to ensure prior compression of the peripheral reservoir.

The starting point for rupture by shearing advantageously corresponds to an annular furrow formed in the plunger, the diameter of said furrow being approximately equal to the internal diameter of the tube.

The gas generator is advantageously a pyrotechnic generator comprising a pyrotechnic charge and a system for initiating said charge.

The injection unit preferably comprises a downstream obturator which includes at least one blind hole forming a burstable leaktight wall, this wall extending between the bottom of this blind hole and the active principle. The injection unit preferably comprises at least one injection tube which penetrates into a blind hole of the downstream obturator and can pierce through the burstable leaktight wall situated between the distal end of this injection tube and the active principle. Each injection tube is advantageously integral with the body of the device.

The liquid active principle is confined in the tube of the reservoir between the upstream plunger and the downstream obturator. When the plunger penetrates into the tube, the pressure produced in the liquid active principle is transmitted to the downstream obturator, which deforms slightly by being pushed back toward the outside of the reservoir, then ends up opening at the level of the burstable leaktight wall, by virtue of each injection tube acting as a rigid punch on said wall. Being integral with the body of the device, the injection tubes are independent of the reservoir and therefore do not risk being subjected to any influence on the part of the moving plunger.

According to another embodiment of the invention, the downstream obturator is made of compressible material so that, under the effect of the pressure generated by the moving plunger, the obturator is crushed at the bottom of the injection device, provoking the piercing of the leaktight wall by the immovable injection tubes.

According to a preferred embodiment off the invention, the downstream obturator extends below the tube and is fitted into the body.

The body advantageously comprises a sole and a compression member which is interposed between the downstream obturator and said sole. This compression member, which can be represented for example by an elastic ring or a spring, acts as a safety means by forming a compressible space preventing each injection tube from bursting the wall of the downstream obturator by fixation of the sole on the injection device. This compressible space also serves as a shock-absorbing device for minimizing the shock due to the impact of the plunger.

The delivery plunger and the downstream obturator are preferably made at least partially of shock-absorbing material. This is because, under the effect of the gases produced by the generator, the plunger will start a movement in the reservoir, which will be translated instantaneously into an internal overpressure which is transmitted to the downstream obturator. As the movement takes place for an extremely brief duration and at a very high speed, there is a considerable risk of pressure wave interferences in the plunger and in the downstream obturator which can lead in particular to a liquid jet being emitted in jolts. Thus, with a view to avoiding this type of disadvantage, it is desirable to attenuate the intensity of the various parasite waves by using shock-absorbing materials which are able to guarantee a uniform and homogeneous thrust of the plunger.

The body preferably comprises a tubular central part, and the sole which is provided with at least one injection tube is connected in a leaktight manner to the central tubular part of said body. In other words, the body of the cutaneous injection device according to the invention consists of a tubular central part and of a sole, and, advantageously, the sole can be likened to a threaded cover which can be screwed around the threaded end of said tubular part.

All the injection tubes are advantageously arranged on the sole in such a way that their axes are oriented in the direction of travel of the plunger in the reservoir.

The gas generator preferably comprises gas evacuation orifices directed at least partially toward the pressurization space. This particular configuration of the evacuation orifices responds to the need to rapidly establish a compression around the reservoir just before the plunger is set in motion. These orifices make it possible to disperse the gas flow in an approximately lateral direction in relation to the axis of the reservoir, and thus to avoid exerting a thrust too early on the plunger.

A sealing joint is advantageously arranged between the downstream part of the body and the injection unit. The gases emitted into the pressurization space cannot therefore invade any free space outside the injection unit, preventing any risk of causing a counter-thrust of said injection unit which could impede the injection.

According to one embodiment of the invention, the downstream obturator includes a peripheral collar in contact with the sealing joint. It is also possible to imagine a downstream obturator made of rubber which has at its periphery a rubber flange, said downstream obturator being able to be engaged in the device in a position in which the flange occupies an annular groove formed in said device and provided for this purpose. For this configuration, the leaktightness is ensured by the flange which is crushed in said groove. For such an embodiment, it is then advantageous that the downstream obturator comprises at least one pre-perforation in line with an injection channel.

Finally, the invention also relates to a method of production, characterized in that:

in a first step, the unit formed by the tubular reservoir filled with the active principle and fitted into the sole equipped with at least one injection tube is protected by a removable leaktight endpiece, all the operations in this first step being carried out under the pharmaceutical conditions of hygiene and safety which are demanded for the production of medicaments, in a second step, this unit is fixed in a leaktight manner to the downstream end of the tubular central part of the body, the other end of which receives the high-pressure gas generator, all of these operations being carried out under simple hygiene and safety conditions.

The injection devices according to the invention, using a device for compression of the reservoir of active principle, have the advantage of being economical and compact. They are compact because the compression device does not exist in storage mode and is created at the start of functioning, in the form of a flow of gas not requiring the involvement of additional solid components specially designed for this compression function. They are economical because the compression device makes use of a pre-existing source of energy and does not need to be integrated in a parallel and autonomous fluid circuit. Finally, the compression device used in the injection devices according to the invention is independent of the position and the speed of the plunger in the reservoir and proves particularly effective while at the same time remaining simple.

A detailed description of four preferred embodiments of the invention is given below with reference to FIGS. 1 through 4.

Figure 1:
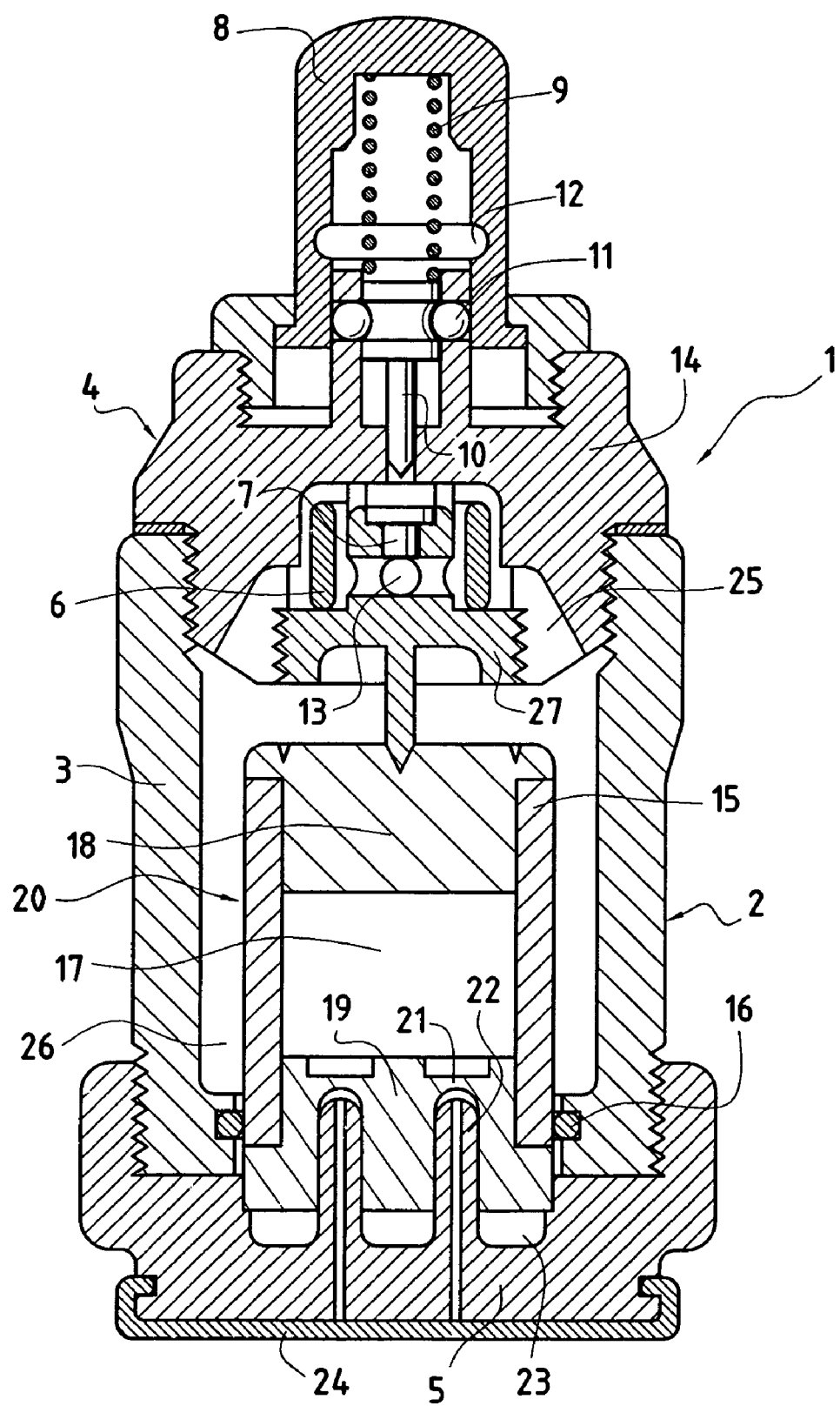
FIG. 1 is a view showing a longitudinal axial cross section through a first preferred embodiment of an injection device according to the invention.

Referring to FIG. 1, an injection device 1 according to a first preferred embodiment of the invention is formed by a body 2 with a tubular central part 3 with two ends, one of them, the upstream end, being intended to receive a pyrotechnic gas generator 4, and the other, the downstream end, being closed off by a sole 5. The pyrotechnic gas generator 4 comprises an initiation device for the pyrotechnic charge 6 which uses a percussion device and a primer 7. The percussion device, which is triggered by a push-button 8, comprises a spring 9 and a striker pin 10. The striker pin 10 is blocked by two balls 11 wedged between said striker pin 10 and the push-button 8, and said push-button 8 has a circular inner groove 12.

The pyrotechnic charge 6, which has a central channel, is arranged around a support 27 containing the primer 7, said support comprising, in the continuation of said primer 7, a hollow part provided with lateral orifices 13. The dimensions of the support are such that there is leaktightness between the space in which the pyrotechnic charge 6 is arranged and the internal space of the support of the primer 7 which can communicate with the internal space of the push-button 8. The striker pin 10 is represented by a cylindrical body, one end of which is pointed, and the other end of which is formed by a widened flat head.

From the structural point of view, the pyrotechnic gas generator 4 comprises a body 14 provided with three threads, one in which the percussion device of the pyrotechnic charge 6 is screwed, a second allowing said body 14 of the generator 4 to be screwed into the tubular part 3 of the body 2 of the injection device 1, and a third thread formed in the ribs which delimit eight gas evacuation slots 25, this third thread permitting attachment of the support 27. This tubular central part 3 has the shape of a hollow cylinder, one end of which is threaded on its inner surface to receive the body 14 of the pyrotechnic gas generator 4, and the other end of which has been bent at a right angle toward the inside of said central part 3, forming, at the area of said end, a passage whose diameter is smaller than the internal diameter of the central part 3. A glass tube 15, with a thickness of 3 mm, whose external diameter of 15 mm is substantially equal to the diameter of said passage, is wedged in the area of this passage by way of a joint 16, one end of said tube 15 reaching the middle of this passage. Situated in continuity with the lateral orifices 13, there are eight evacuation slots 25 which have a progressive curvature and join the inner lateral wall of the tubular central part 3 of the body 2. Said tube 15 which is intended to contain the liquid active principle 17 is, on the one hand, closed off at its upstream part by a plunger 18 comparable to a stopper with a widened flat head emerging from the tube 15, said head having diameter approximately equal to the external diameter of the tube 15 and having, on its flat outer surface, a starting point for rupture by shearing in the form of an annular furrow whose diameter is approximately equal to the internal diameter of the tube 15, and, on the other hand, is closed off at its downstream part by a downstream obturator 19.

The assembly comprising "glass tube 15, plunger 18 and downstream obturator 19" constitutes the reservoir 20 of the liquid active principle 17. The downstream obturator 19 is also comparable to a stopper with a widened flat head emerging from the tube 15, said head having a diameter approximately equal to the external diameter of the tube 15 and having four blind holes on its outer plane surface. The downstream obturator 19 has an inner plane surface in which an annular groove has been formed in such a way that the four blind holes, which are uniformly spaced, are distributed in a crown having the same dimensions as that formed by the groove. The thickness of the downstream obturator 19 is thus reduced in the area of the annular groove corresponding to the blind holes, making it possible to define a burstable leaktight wall 21 isolating the liquid active principle 17 from the blind holes.

The sole 5, which is comparable to a threaded cover, is screwed around the tubular central part 3. Said sole 5 has an inner circular plane face comprising a cylindrical central recess with an inner shoulder distinguishing a shallow part with the same diameter as that of the widened head of the downstream obturator 19 and a deep part with a reduced diameter. The downstream obturator 19 is positioned in the injection device in such a way that it closes off the tube 15 and the outer lateral surface of the widened head comes to bear both against the bent edge of the tubular central part 3 of the body 2 and the inner lateral wall of the shallow part of the cylindrical central recess of the sole 5, said inner wall of the shallow part being situated in continuity with the bent edge. The widened head of the downstream obturator 19 thus occupies the entire shallow part of the recess although it abuts against the inner shoulder of said cylindrical central recess of the sole 5. The lower part of the recess of the sole 5 has a bottom from which four elongate protuberances emerge, each of these protuberances being traversed along their length by a channel which opens out, on the one hand, outside of said protuberance and, on the other hand, outside the sole 5. These channeled protuberances constitute injection tubes 22. Said injection tubes 22, which are integral with the sole 5 and whose axes are parallel to that of the tube 15 of the reservoir 20, occupy the blind holes of the downstream obturator 19. The lower part of the recess of the sole 5 is formed, between the injection tubes 22, by a free space 23. The sole 5 has an outer circular plane face in which the through-channels of the injection tubes 22 open, said circular face being covered by a leaktight removable endpiece 24. The reservoir 20 of liquid active principle, which is fixed in the area of its downstream part to the body 2 of the injection device 1, leaves a free space 26 situated between its outer lateral wall and the inner lateral wall of the tubular central part 3 of the body 2 in which it is accommodated. This free space 26 is situated in communication with the eight evacuation slots 25, which are themselves in communication with the pyrotechnic charge 6.

The method of functioning of this first preferred embodiment of the invention is as follows.

The user takes off the removable leaktight endpiece 24 which serves to protect the injection device 1.

He positions the injection device 1 in such a way that the sole 5 comes to bear against the skin of the patient to be treated. A pressure applied to the push-button 8 allows it to slide along the syringe until the groove 12 comes into line with the balls 11 blocking the striker pin 10. A spring 9 placed in the syringe confers a certain resistance to the push-button 8 so as to compel the user to exert a particular force to depress said push-button 8. As the balls 11 are then no longer wedged, they free the striker pin 10 which, under the effect of the spring 9 which is released, is propelled toward the primer 7. The primer 7 which is then initiated provokes the firing of the pyrotechnic charge 6 by way of the lateral orifices 13. The gases produced by the combustion of the pyrotechnic charge 6 pass through the evacuation slots 25 and instantaneously invade the pressurization space 26 which simultaneously provokes, on the one hand, the external compression of the tube 15 and the internal compression of this tube by the pressure which is exerted on the plunger 18 made of elastomer, and, on the other hand, the displacement of the reservoir 20 in the free space 23 by compression and deformation of the downstream obturator 19 made of elastomer. Once the pressure exerted on the plunger 18 reaches a threshold value, said plunger 18 yields at the level of its starting point for rupture by shearing and begins to displace in the tube 15 and exert a thrust on the liquid active principle 17. The downstream obturator 19 is then in contact with the inner plane face of the sole 5 and the injection tubes 22 each acting as a punch burst the wall 21. The liquid active principle 17 then invades the channels of said tubes 22 before being injected into the patient.

Figure 2:
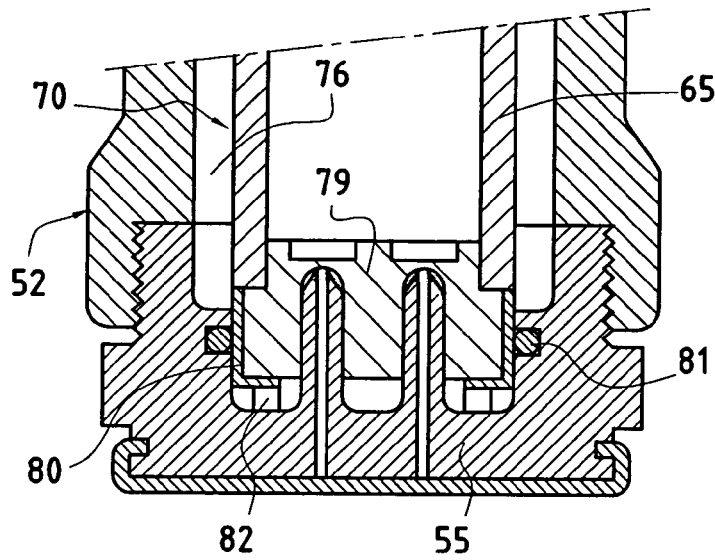
FIG. 2 is a view showing an axial cross section through the end part of a second preferred embodiment of an injection device according to the invention.

Referring to FIG. 2, an injection device according to a second preferred embodiment of the invention differs from the first preferred embodiment described above in terms of the configuration of the downstream obturator 79 and the sole 55, and the fixation of the reservoir 70 of the body 52 of the injection device. A part of the widened head of the downstream obturator 79, which is partially covered by a metal collar 80 with shoulder, is inserted in a cylindrical recess of the sole, the leaktightness of this contact being provided by means of a joint 81 wedged between said collar 80 and the inner lateral wall of the recess. A compression member 82 formed by an undulated metal washer is interposed between the head of the obturator 79 and the bottom of the recess in which it is inserted. This compression device 82, which can have the form of a spring or a compressible ring, means that the obturator 79 can be held in a given position and it also serves as a safety device Guaranteeing an incompressible space between the obturator 79 and the sole 55 in order to avoid bursting said obturator 79 when the gas generator has not been triggered. Once inserted in said recess, the widened head of the obturator 79 emerges from said recess, although the tube 65 of the reservoir 70 which abuts against the widened head is isolated from the body 52 of the injection device.

The method of functioning of an injection device according to this second preferred embodiment of the invention is in every point identical to that described for the first preferred embodiment of the invention.

The arrangement of the components involved in this second preferred embodiment of the invention makes it possible to avoid any direct contact between the glass reservoir 70 and the solid body 52 of the injection device, which contact could be prejudicial for said reservoir 70 which is susceptible to breaking by rubbing or bearing against a solid surface, for example if the injection device is dropped during handling or in the event of defective storage.

Figure 3:
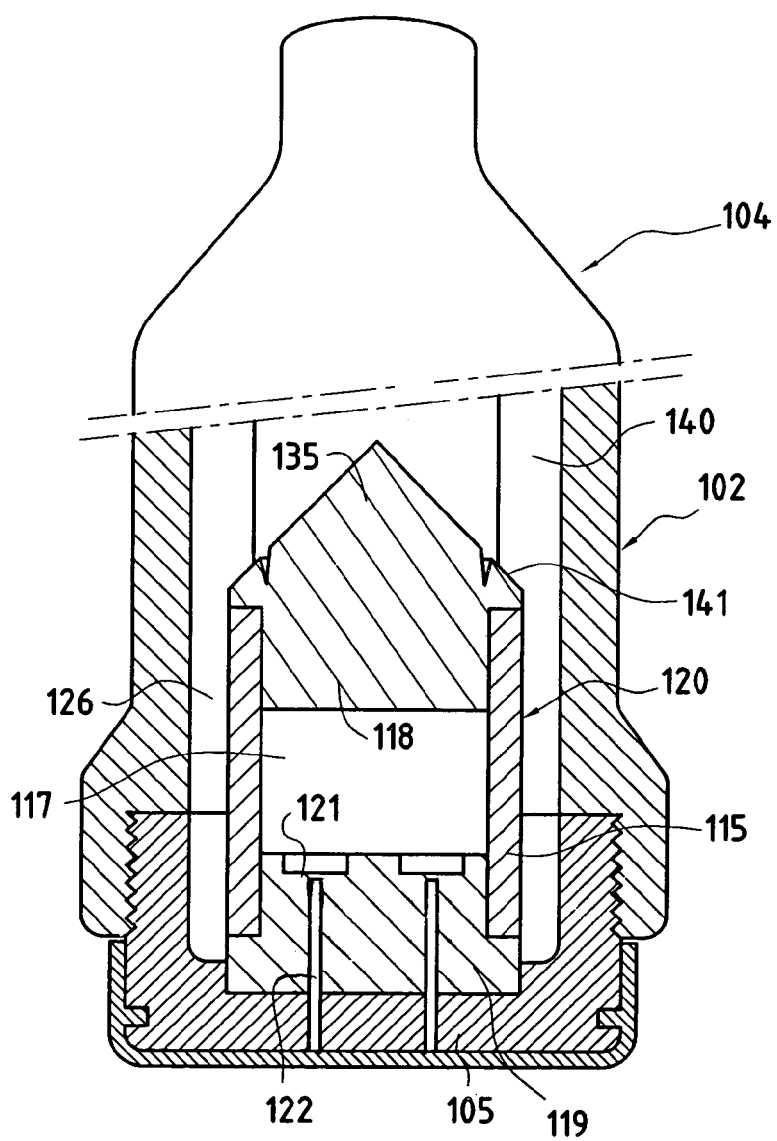
FIG. 3 is view showing a partial axial cross section through a third preferred embodiment of an injection device according to the invention.

Referring to FIG. 3, an injection device according to a third preferred embodiment of the invention differs from the first embodiment on the points described below. The gases emitted by the pyrotechnic gas generator 104, of which only the contour has been indicated, are no longer diffused transversely in the body 102 of the injection device by way of lateral orifices, but are instead produced along the axis of said body 102 and thus arrive at the reservoir 120 in a direction parallel to its axis of revolution. Said reservoir 120 is fixed in the body 102 of the device by way of four longitudinal centering ribs 140 arranged on the inner wall of said body 102 and forming an angle of 90° relative to one another, said ribs 140 having a shoulder 141 for longitudinal wedging of the reservoir 120. The downstream obturator 119, which is made of a compressible material and which closes off the tube 115 of the reservoir 120, bears against the plane bottom of a recess formed in the sole 105 of the body 102. The widened head of the obturator 119 emerges from the recess and the tube 115 which abuts against said head is isolated from the body 102. The plunger 118 which closes off the upstream end of the tube 115 emerges from said tube 115, the emerging part 135 of the plunger 118 having a conical shape whose widened base, which abuts against the tube 115, has a diameter greater than the external diameter of said tube 115 in order to ensure centering with shock absorption and to come into contact with the wedging shoulder 141 of the ribs.

The method of functioning of this third preferred embodiment is as follows. The user fires the pyrotechnic charge by acting as in the manner described for the first preferred embodiment of the invention. The gases emitted arrive at the conical part 135 of the plunger 118, which acts as a deflector favoring the diffusion of said gases around the reservoir 120, which is then exposed to a slight over-compression which compensates for the internal pressure due to the deformation of the rubber plunger 118 which initiates a movement in the reservoir 120. The flexible obturator 119 crushes and it opens its leaktight wall 121 by way of the injection tubes 122 punching said wall 121. The liquid active principle 117 is then expelled via the channels of the injection tubes 122 until the central part of the plunger 118 comes into contact with the obturator 119.

Figure 4:
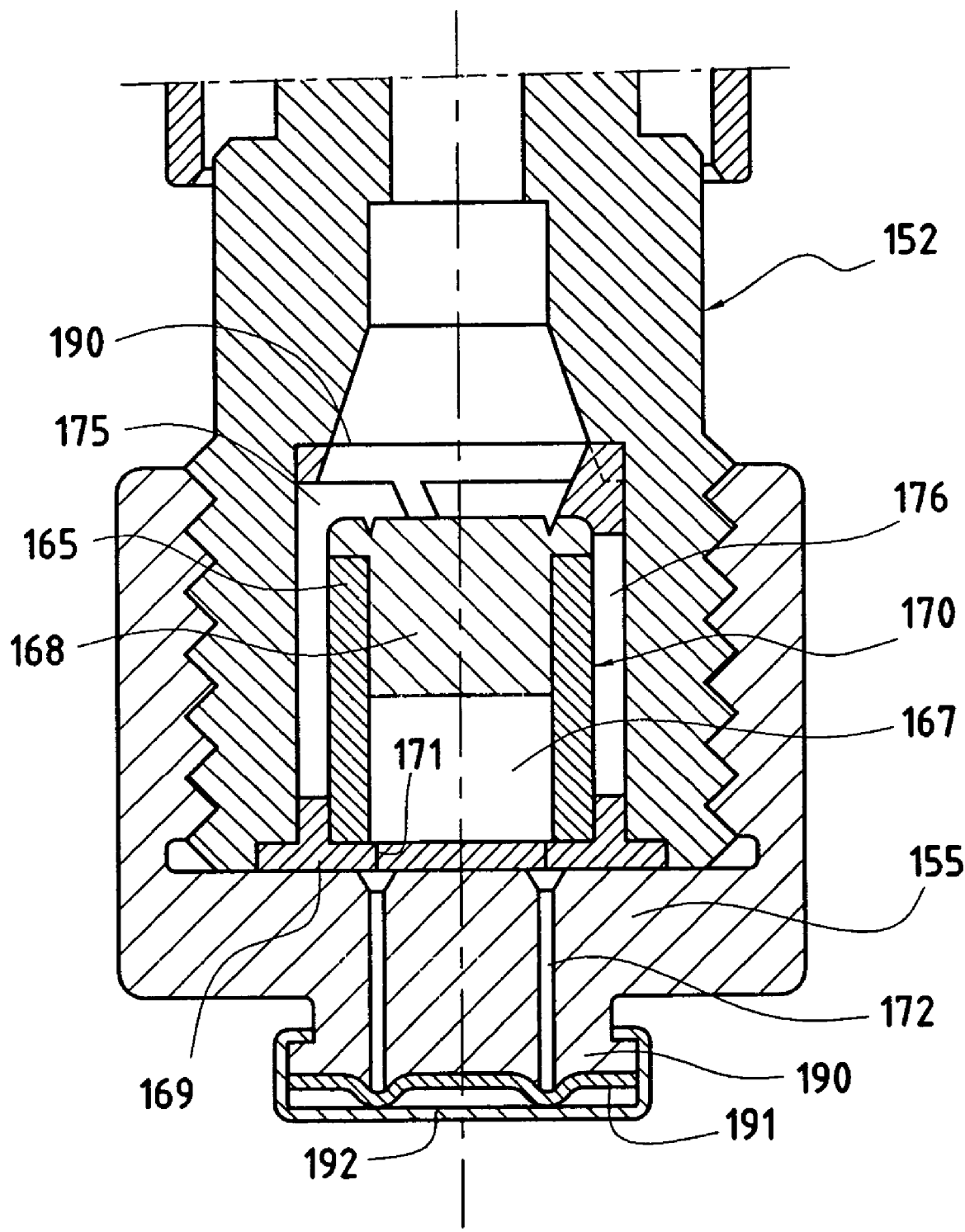
FIG. 4 is a view showing an axial cross section through the end part of a fourth preferred embodiment of an injection device according to the invention.

Referring to FIG. 4, an injection device according to a fourth preferred embodiment of the invention differs from the first embodiment in the points described below. The gases emitted by the generator (not shown in the figure) are produced along the axis of the body 152 of the injection device, said body 152 having a central channel with a progressive widening 190 situated upstream of the reservoir 170. This widening 190 is divided into compartments by means of three ribs providing for the wedging of the tubular reservoir 170 and determining three wide openings 175 in such a way as to allow the flow of the gases around the reservoir 170 in the pressurization space 176. The downstream obturator 169 is made of rubber and has the shape of a hollow cylinder of low height, closed at one of these two ends by a disk whose diameter is greater than the external diameter of said cylinder. Said obturator 169 is interposed between the reservoir 170 of liquid active principle 167 and the sole 155 of the body 152, in such a way that, on the one hand, the hollow cylinder of said obturator 169 ensures wedging and leaktightness between the outer lateral wall of the tube 165 and the inner lateral wall of the body 152 and, on the other hand, the disk of said obturator 169 rests in contact with the sole 155 by having its peripheral part wedged in a leaktight manner between the body 152 and said sole 155. The surface of the sole 155 which is in contact with the disk of the obturator 169 has at its surface four conical indents at the bottom of which injections channels 172 start which pass through the sole 155. The sole 155 has a terminal projection 190 in which said channels 172 open. The disk of the obturator 169 comprises four pre-perforations 171 in the area of the zones corresponding to the conical indents of the sole 155. The terminal projection 190 is closed off by an elastomeric layer 191 and a metal cap 192 crimped around said terminal projections 190. The method of functioning of this fourth preferred embodiment is as follows.

The user removes the layer of elastomer 191 and the metal cap 192 serving as protection for the injection device. He then places the terminal projection 190 against the skin of the patient who is to be treated. He then fires the pyrotechnic charge by acting in the manner described for the first preferred embodiment of the invention.

The gases emitted arrive at the plunger 168 at the same times as they invade the pressurization space 176 via the evacuation openings 175, thus instantaneously compressing the reservoir 170. When the pressure is sufficient to burst its outer flange, the plunger 168 commences a movement in the reservoir 170, creating an internal overpressure which opens the downstream obturator 169 in the area of its four pre-pierced zones. The liquid active principle 167 is then expelled at very high speed through the channels 172, passing through the sole 155 toward the skin of the patient who is to be treated.

The invention claimed is:

1. A cutaneous injection device, comprising:
   a body having an inner wall, the body being intended to inject a liquid active principle contained in a tubular reservoir, the tubular reservoir formed by a tube, which is closed at its upstream end by a delivery plunger and which has, at its downstream end, an injection unit, the tubular reservoir being lodged in the body of the injection device, the tubular reservoir being disposed in a space defined by the inner wall;
   a high-pressure gas generator upstream of the delivery plunger, which makes it possible to exert a pressure on the delivery plunger; and,
   a space for pressurization by the gases of the generator is delimited by and directly adjacent to both the outer wall of the tubular reservoir and the inner wall of the body,
   wherein the delivery plunger extends above the tube and the plunger includes a starting point for rupture by shearing which corresponds to the internal dimensions of the tube.

2. The device as claimed in claim 1, further comprising:
   a downstream obturator, which includes at least one blind hole forming a burstable leaktight wall, this wall extending between the bottom of the blind hole and the liquid active principle.

3. The device as claimed in claim 2, wherein the downstream obturator extends below the tube and is fitted into the body.

4. The device as claimed in claim 3, wherein the body includes a sole, and a compression member interposed between the downstream obturator and said sole.

5. A method for producing a cutaneous injection device as claimed in claim 4, the method comprising:
   protecting the tube fitted into the sole equipped with the injection unit with a removable leaktight endpiece, this protecting being carried out under the pharmaceutical conditions of hygiene and safety which are demanded for the production of medicaments; and
   fixing the injection unit in a leaktight manner to the downstream end of the of the body, the upstream end of which receiving the high-pressure gas generator, all of these assembly operations being carried out under simple hygiene and safety conditions.

6. The device as claimed in claim 3, wherein the downstream obturator includes at least one pre-perforation in line with an injection channel.

7. The device as claimed in claim 2, wherein the delivery plunger and the downstream obturator are made at least partially of shock-absorbing material.

8. The device as claimed in claim 1, wherein the inner wall of the body includes at least three longitudinal ribs for centering the tubular reservoir.

9. The device as claimed in claim 1, wherein the tube is made of glass.

10. The device as claimed in claim 1, wherein the outer surface of the delivery plunger, directed toward the gas generator, constitutes a deflector for deflecting the gases toward the pressurization space.

11. The device as claimed in claim 1, wherein the gas generator is a pyrotechnic generator.

12. The device as claimed in claim 1, wherein the gas generator includes gas evacuation orifices directed at least partially toward the space for pressurization.

* * * * *